(12) United States Patent
Khouri et al.

(10) Patent No.: US 10,580,521 B1
(45) Date of Patent: Mar. 3, 2020

(54) EMERGENCY INFORMATION AND IDENTIFICATION DEVICE AND METHOD

(71) Applicant: Medris, LLC, Charlotte, NC (US)

(72) Inventors: George Khouri, Charlotte, NC (US); Jeffrey Bodle, Cornelius, NC (US)

(73) Assignee: MEDRIS, LLC, Charlotte, NC (US)

( * ) Notice: Subject to any disclaimer, the term of this patent is extended or adjusted under 35 U.S.C. 154(b) by 535 days.

(21) Appl. No.: 15/217,451

(22) Filed: Jul. 22, 2016

Related U.S. Application Data

(60) Provisional application No. 62/195,411, filed on Jul. 22, 2015.

(51) Int. Cl.
  *G16H 10/60* (2018.01)
  *G06F 19/00* (2018.01)
  *G06K 9/00* (2006.01)

(52) U.S. Cl.
  CPC .......... *G16H 10/60* (2018.01); *G06F 19/328* (2013.01); *G06K 9/00087* (2013.01); *G06K 9/00288* (2013.01); *G06K 9/00617* (2013.01)

(58) Field of Classification Search
  None
  See application file for complete search history.

(56) References Cited

U.S. PATENT DOCUMENTS

| | | | |
|---|---|---|---|
| 6,131,090 A | 10/2000 | Basso, Jr. et al. | |
| 7,426,475 B1 | 9/2008 | Tangellapally et al. | |
| 8,346,575 B2 | 1/2013 | Meagher | |
| 8,689,005 B2 | 4/2014 | Lentini | |
| 2002/0083192 A1 | 6/2002 | Alisuag | |
| 2011/0276350 A1 | 11/2011 | Khanal | |
| 2012/0023592 A1 | 1/2012 | Wilson | |
| 2013/0173284 A1* | 7/2013 | Hyde | G06Q 50/22 705/2 |
| 2013/0197941 A1 | 8/2013 | Cochran | |
| 2013/0318359 A1 | 11/2013 | Morris et al. | |
| 2013/0318361 A1 | 11/2013 | Erickson et al. | |
| 2013/0325511 A1* | 12/2013 | Neagle, III | G06Q 50/24 705/3 |
| 2014/0081667 A1* | 3/2014 | Joao | G06F 19/328 705/3 |
| 2014/0299662 A1 | 10/2014 | Harrison | |

FOREIGN PATENT DOCUMENTS

WO  WO2014011633  1/2014

* cited by examiner

*Primary Examiner* — Michael Tomaszewski
(74) *Attorney, Agent, or Firm* — Alston & Bird LLP

(57) ABSTRACT

A mobile computing device is equipped with an optical scanner that captures a physical feature of a person, and/or reception of a unique identification code transmitted from a wearable signal emitter. The mobile computing device converts the optical scan to digital data that is transferred to a remote server. The remote server contains personal information about a plurality of people. The remote server compares the digitized optical information and/or unique identification code with stored information about the person from whom the optical scan was taken. The server compares the digitized optical scan and/or unique identification code with the associated digital information on the server, and if the information matches; the server transmits healthcare related information about the specific person to the mobile computing device.

10 Claims, 3 Drawing Sheets

EMERGENCY INFORMATION AND IDENTIFICATION DEVICE AND METHOD

Applicant claims the benefit of Provisional Application Ser. No. 62/195,411 filed Jul. 22, 2015.

FIELD OF THE INVENTION

This invention relates to communications devices generally and is more specifically related to devices and methods of communicating information in the healthcare setting.

BACKGROUND OF THE INVENTION

Currently, in the United States, and many other countries throughout the world, there is no secure or digital access to personal health related information, such as, but not limited to, medical history, hospitalizations, hospital and physician notes, medications, allergies, emergency contacts, home healthcare system, physician name, blood types, advance directives or other important personal information in an emergency medical situation outside of a hospital or similar comprehensive healthcare facility. The absence of readily available information leads to unnecessary and potentially avoidable medical errors, and sub-optimal healthcare administration. The implementation of electronic health records (EHR) in the United States has led to a heterogeneous system of health information record storage and software, which do not allow for efficient inter-hospital and inter-provider transmission. The current lack of inter-hospital information accessibility has also lead to a lack of access to end-of-life and scope of treatment wishes, such as those found in legally recognized advance directives. Patients may be subjected to undesired emergency and inpatient hospital care, which could be reduced or avoided by through improved communication and transfer of important personal information.

There is a need for a device and method of providing the efficient transfer of personal information, especially where information is required regarding a person who is unable to speak or otherwise adequately communicate due to his or her physical condition. The device and method must provide secure and verifiable identification of the person and his or her personal information.

SUMMARY OF THE INVENTION

A mobile computing device is equipped with an optical scanner that captures a physical feature of a person, and/or reception of a unique identification code transmitted from a wearable signal emitter. The mobile computing device converts the optical scan to digital data that is transferred to a remote server. The remote server contains personal information about a plurality of people. The remote server compares the digitized optical information and/or unique identification code with stored information about the person from whom the optical scan was taken. The server compares the digitized optical scan and/or unique identification code with the associated digital information on the server, and if the information matches, the server then transmits healthcare related information about the specific person to the mobile computing device.

BRIEF DRAWING DESCRIPTION

Figure 1:
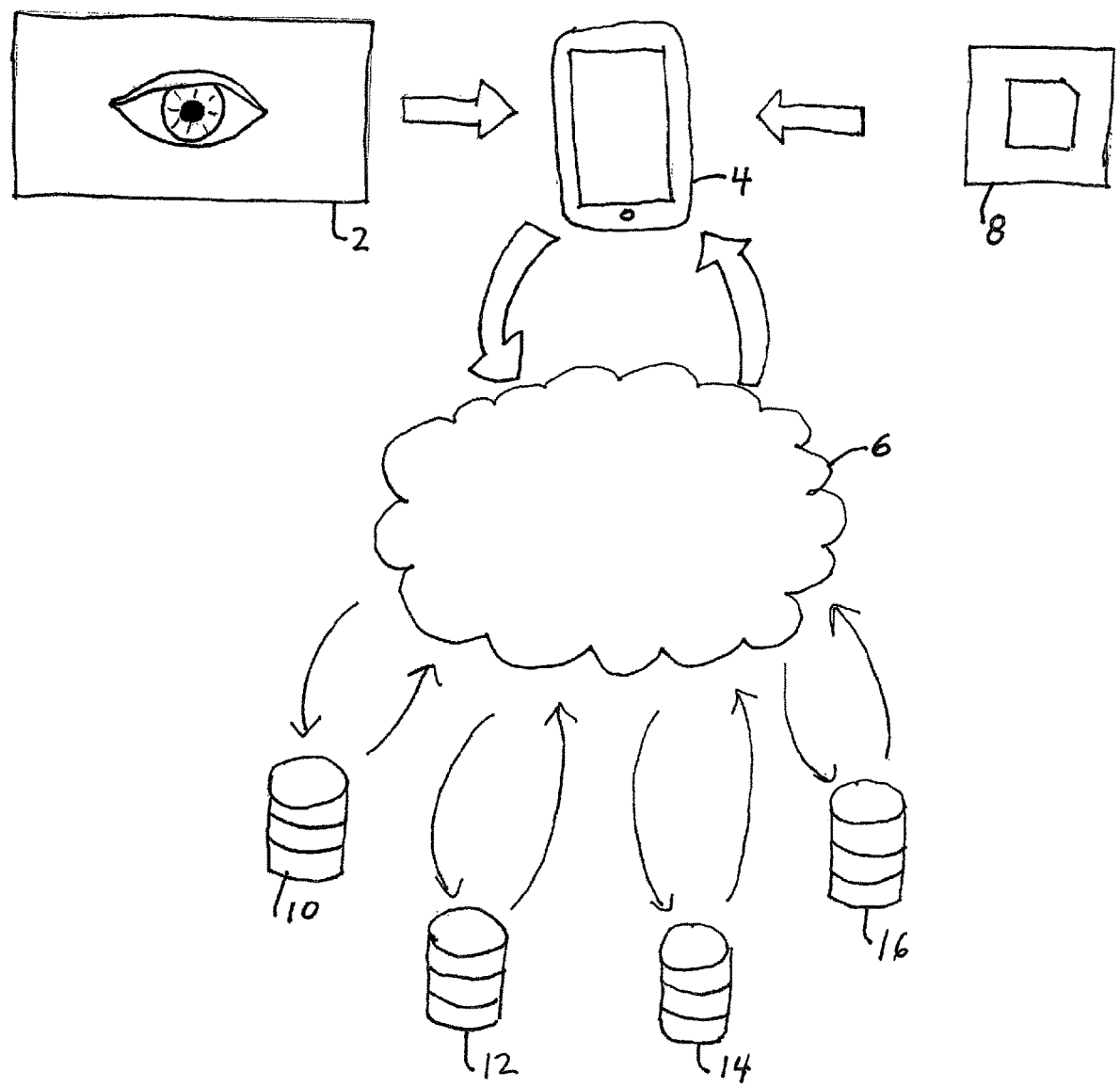

FIG. 1 demonstrates an embodiment of the invention comprising a biometric scanning device and a wearable emitter that communicate with a mobile computing device that in turn communicates with a cloud server and associated databases.

Figure 2:
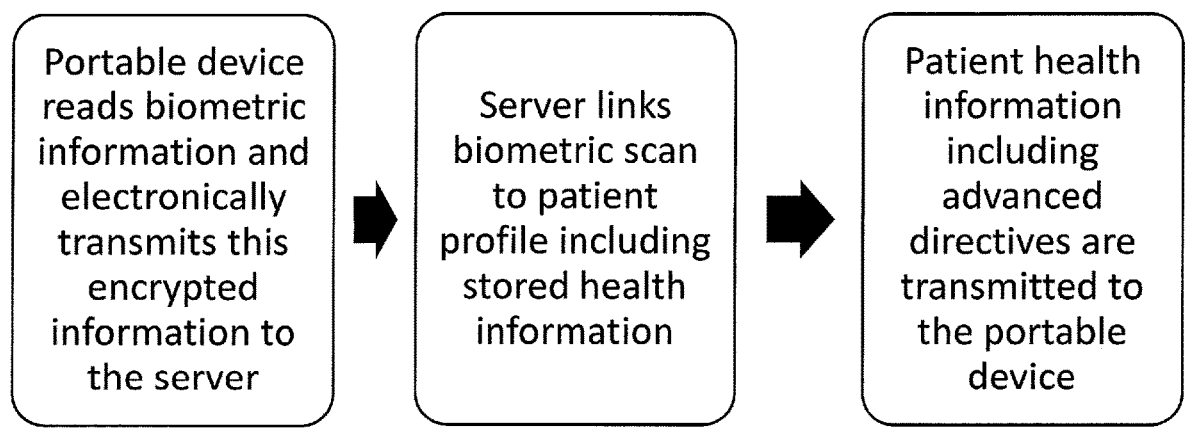

FIG. 2 is a schematic showing method steps according to an embodiment of the invention.

Figure 3:
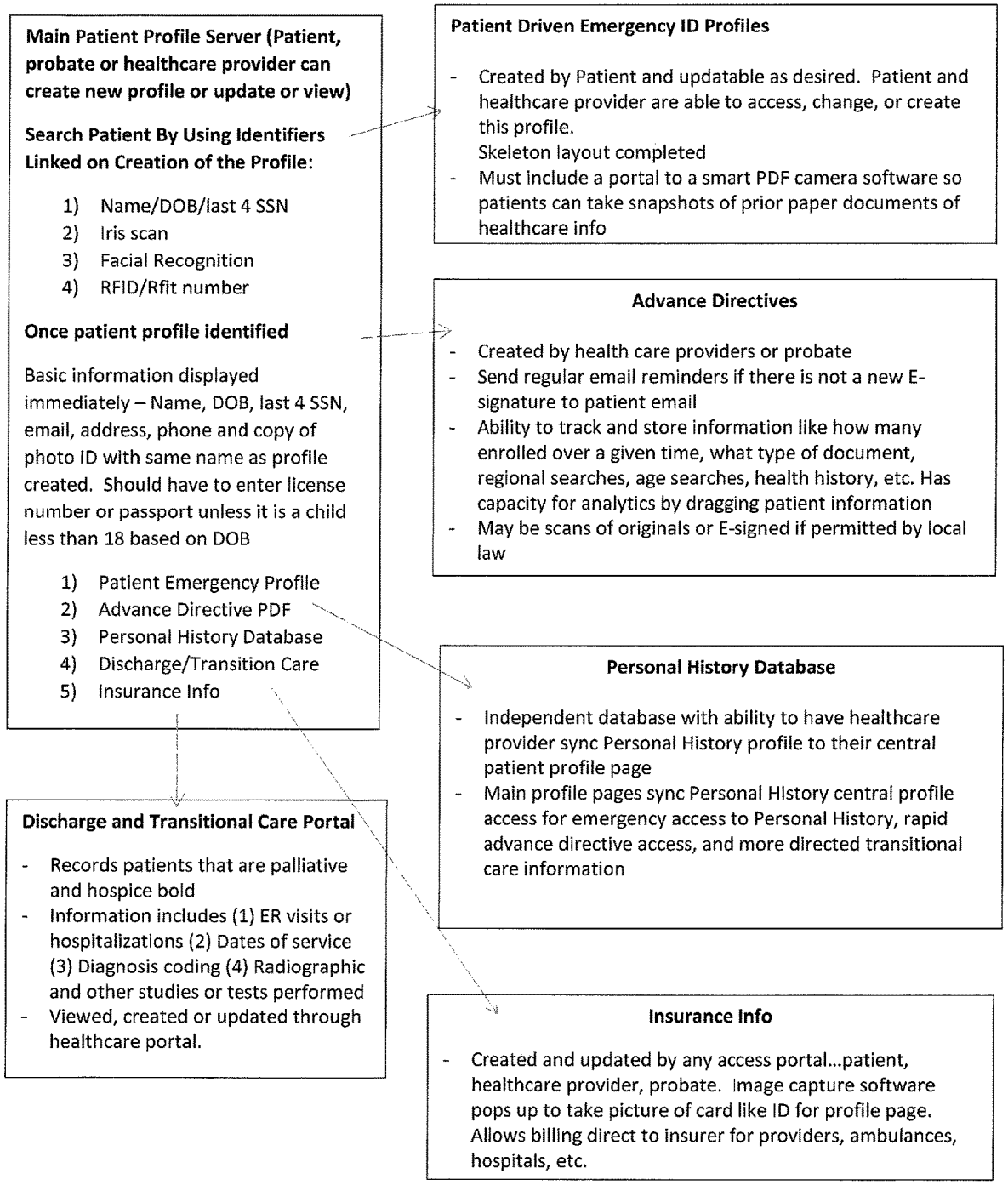

FIG. 3 demonstrates an exchange of information between databases.

DESCRIPTION OF PREFERRED EMBODIMENTS

In an embodiment of the device, a mobile computing device is equipped with an optical scanner 2 that captures a physical feature of the person, such as a biometric. For example, the optical scanner captures an image of a person's face, a scan of a person's iris or retina, or a person's fingerprints or toe prints.

The mobile computing device converts the optical scan to digital data that is transferred to a remote server by wire or, preferably, wireless communication link. The mobile computing device 4 may be a cellular telephone or "smart" phone, a tablet-computing device, or a notebook computer, by way of example. The primary requirements of the mobile computing device are that it comprises or communicates with an optical scanner 2 that digitizes the information captured by the optical scanner, and that the mobile computing device is able to communicate with a remote or cloud server 6. FIG. 1; FIG. 2.

The remote server 6 contains or accesses personal information about a plurality of people. The remote server has the capability to compare the digitized optical information with information about the person from whom the optical scan is taken. The remote server also contains the same or analogous digital information about the physical feature or biometric of the person with whom it personal information is associated. The server compares the digitized optical scan with the associated digital information on the server, and if the information matches, the server then transmits the information to the mobile computing device 4.

The digitized physical information about the person contained on the remote server corresponds to the information scanned from the mobile computer device. For example, if an iris scan is taken by the mobile computing device, then corresponding information about the person's iris is stored on the remote computer.

In another embodiment, the invention comprises a wearable communications device 8. FIG. 1. The wearable device compresses an emitter that actively emits a signal that is received by a receiver that is within a few meters of the emitter. The emitter emits an identification signal that is unique to the emitter, and to the person wearing the emitter. The emitter may be an active radio frequency identification device (RFID). By wearable, it is meant a device that can be configured to accompany a person without material interference with the person's activities. For example, a wearable RFID device may be worn as a wristwatch, positioned on a tag worn about the neck, worn as jewelry, or placed in a wallet or in a pocket or purse of a person. An RFID device in this embodiment comprises a Unique Identification (UID), and need not contain any other information, although it may contain other information. By minimizing the amount of data stored, the RFID device may be of extremely small size. Further, since only a minimal data, such as an alphanumeric string, is the only data transmitted, there is no personal or confidential information about the person transmitted by the emitter. Further security is provided by using a combination of the identification emitter, such as RFID or NFC devices, as described along with the optical physical recognition device. Further security is provided by using a combination of the emitter as described along with the physical recognition device.

In this embodiment, the RFID device communicates the unique identification to a receiver. The receiver may be part of a mobile computing device. The receiver transmits the unique identification in a digital form to the remote server. As with the prior embodiment, the remote server compares the UID with a unique identification that corresponds to personal information regarding the person to whom the UID is assigned. Upon ascertaining a match, the remote server transmits personal information about the wearer of the emitter to the mobile computing device.

In another embodiment, the receiver is placed within an ambulance, gurney or other patient transport device. As soon as the patient is place on the gurney or within the ambulance or helicopter, the receiver receives the RFID or other signal and transmits it to the remote server. A visual display that may be associated with a mobile computing device or a computer within the transport device displays information to medical personnel who are on the scene.

Near Field Communications (NFC) devices transmit information to other devices, such as mobile computing devices, that are fairly nearby, and usually up to a distance of about four (4) centimeters. The risk of transferring information in an undesired manner is minimized. A Near Field Communications (NFC) device may be the wearable emitter as described herein.

In an embodiment, the remote server compares both the information received from the digitized optical scan of the person's physical features and the UID, and only releases the personal information and transmits it to the remote computing device if there is a satisfactory match of the UID and the digitized physical feature of the person.

In an embodiment, a data profile of physical or medical information about a person is established, such as by a healthcare professional. The data profile may contain personal information about the person's medical history, family history, hospitalizations, hospital and physician notes, medications, allergy information, emergency contacts, insurance information, home health care provider, primary physician and/or other physician names, blood type, copies of advance medical directives (such as a living will, durable power of attorney), and other health information that may be useful to a caregiver, particularly in an emergency medical setting. The information may be presented as scans of original documents. The information is particularly useful in an urgent care situation where the person is non-communicative, or otherwise is unable to speak.

The data profile of medical information may be contained in a Personal History database 10. The Personal History database may be a compendium compiled from past medical records obtained from healthcare providers. Notably, it is preferred that the database comprise information from insurance companies regarding medical services and procedures paid for by insurance. This information may alert the healthcare professional to preexisting conditions that would otherwise not be discovered, especially in an emergency setting. This information may also prevent the healthcare professional from unnecessarily performing time consuming and/or expensive tests or procedures that were previously performed. Rather, the healthcare professional can refer to the medical records available in the personal history. Preferably, the insurance billing history is synchronized in the Personal History database with the medical records and medical history obtained from providers.

In establishing the data profile, it is preferred that at a minimum, the person who uses the profile will provide information as described above. Optionally, other information may be provided by health care providers or insurance companies. Specific medical records from physicians and hospitals may be provided.

In use, and by way of example but not exclusion, a person who is in need of urgent medical care due to trauma, disease, or otherwise, may be scanned by the mobile computing device, either to obtain physical information or biometrics about the person for identification purposes or to obtain a UID from the NFC device as described. Identification of the person is quickly provided to the remote server, and upon authentication of the identifying information from the remote computing device, the remote server provides information about the person to the treating medical professional. It is preferred that a consistent format of the information be provided to the medical professional, so that the medical professional can quickly ascertain relevant information.

The quick transfer of information between the identification emitter, if used, and/or the optical physical scanning device, the mobile computing device and the remote server means that critical information can be ascertained about the person within seconds. The ability to obtain information may be critical where the person is non-communicative or uncooperative upon presentation, but the device allows important information to be quickly obtained by a medical professional in a logical and consistent format even where the person is cooperative. Valuable and critical time may be saved.

The device can eliminate unnecessary medical procedures as indicated by a person's medical history. Further, information that may be important to life saving or quality of life decisions may be provided.

The device as described above accesses one or more databases, and provides information to medical personnel. The databases may include a database of personal information, typically compiled by or for the subject; personal medical history database as compiled from medical records created by medical providers; a database as compiled from records of health insurance entities, whether public or private; and a database having important person legal documents therein. Some of the information may be redundant.

The subject person, or patient, may have a portal (Patient Portal) that grants access to his or her profile and personal information, such as date of birth, government issued identification numbers (for example, driver's license or passport number), photograph, address, insurance information and other unique information that is unique to the person. Some of the information may be changed, such as the current health insurance information, whereas other information may not be changed but may be viewed. Each portal described may access multiple databases as described above, with privileges to view or modify as appropriate to the portal.

The Patient Portal is stored on a central server in one embodiment. The Patient Portal has access to other other databases. FIG. 3. These databases may include an Advance Directive database 12, Emergency Identification database 14, Personal History database 10, and/or a Hospital Discharge/Transitional care database 16. Portals in the form of apps or icons and specific to certain providers who have access to either view, create, or change the information in the particular database and for the particular person.

The Patient Portal may be accessed, for example, by e-mail or a website, or by an app. The Patient Portal allows the user to access a General Main profile page. Some information may be changed from the portal. An emergency profile with emergency information such as contact information may be accessed and changed in most cases. Advance directives may be viewed, but typically may not be changed. Transition and discharge care, as well as particular detailed medical information would not typically be accessible from the Patient Portal.

The Healthcare Portal provides access that is generally universal. Medical providers, hospice, Emergency Medical Technicians and other may use this portal for general database access. The General Main Profile page (with identifying information), Advance Directives data, Emergency profile, and Transition Care/Discharge information data may be accessed, viewed and changed. The Personal History Database may be synchronized with other databases pertinent to the patient through this portal.

The Legal Information Portal provides access to the patient's advance directives. Typically, there is no access to the patient's Personal History, Transition Care/Discharge information or other health information about the patient. This portal allows the healthcare professional to review a living will, a durable power of attorney and other patient directives involving legal matters. The patient and/or his or her attorney may have access through this portal.

The Transition Care/Discharge information may comprise: 1) the identity of the hospital/provider system; 2) an ER visit or hospitalization; 3) date of service; 4) diagnosis; 5) treatment; and/or 6) tests performed or studies done, such as radiology or other imaging.

In use, according to an embodiment, the emitter communicates a UID to a mobile computing device that receives the UID in a signal generated by emitter, which may be a radio frequency (RF) emitter or NFC device. The mobile computing device and/or an associated device additionally or alternatively capture a physical feature of the person, such as an iris scan, facial photograph or fingerprint(s). The mobile computing device transmits the UID and/or the physical feature to a central server. If the UID and/or the physical feature are verified to relate to the same person, the process is authenticated, and access to the person's information, or Patient Portal, is "unlocked". It is preferred that both the UID and physical feature are used, since requiring both forms of identification significantly reduces the chance of error in identifying the person. Information from the Patient Portal, such as profile and personal information as described above, is transmitted to the mobile computing device.

Unlocking of the Patient Portal also provides access to the other portals and associated databases as described above. The healthcare professional has access to view the Personal History database, Advance Directives database, Emergency Information database, and Insurance database. FIG. 3. Selected information is transmitted from the server to the mobile computing device in an emergency setting, such as a trauma site, or other computing device, such as in a hospital setting. The healthcare professional may have access to modify or add to selected information in a database as described herein.

What is claimed:

1. A system for providing secure and verifiable identification of a person, comprising:
   a mobile computing device, the mobile computing device comprising an optical physical recognition device and a receiver, wherein the receiver is placed within an ambulance;
   a wearable signal emitter associated with the person that emits a signal, wherein the signal comprises a unique identification code and is receivable by the receiver of the mobile computing device; and
   a remote server that communicates with the mobile computing device;
   wherein the optical physical recognition device is configured to:
      capture a physical feature of the person, and
      convert the physical feature to digital information;
   wherein the receiver is configured to:
      when the person is in the ambulance, receive the unique identification code from the wearable signal emitter;
   wherein the mobile computing device is configured to:
      subsequent to converting the physical feature to the digital information via the optical physical recognition device and receiving the unique identification code via the receiver, communicate the digital information of the physical feature and the unique identification code to the remote server, and
   wherein the remote server is configured to:
      compare the digital information of the physical feature and the unique identification code;
      determine that both the digital information of the physical feature and the unique identification code are related to the same person;
      in response to determining that both the digital information of the physical feature and the unique identification code are related to the same person, identify personal health related information about the person stored on the remote server by at least one of the digital information of the physical feature or the unique identification code, wherein the personal health related information comprises an identity of hospital system associated with the person; and
      transmit the personal health related information to the mobile computing device.

2. A system for providing secure and verifiable identification of the person as described in claim 1, wherein the remote server accesses databases having information about health insurance and advance directives associated with the person, and transmits the information about health insurance and advance directives associated with the person to the mobile computing device.

3. A system for providing secure and verifiable identification of the person as described in claim 1, wherein the wearable signal emitter emits a radio frequency signal and transmits information received by the mobile computing device.

4. A system for providing secure and verifiable identification of the person as described in claim 1, wherein the wearable signal emitter is a near field communications device that transmits information received by the mobile computing device.

5. A system for providing secure and verifiable identification of the person as described in claim 1, wherein the remote server accesses databases having information about transition care associated with the person upon discharge from a healthcare provider, and transmits the information about transition care associated with the person upon discharge from the healthcare provider to the mobile computing device.

6. A system for providing secure and verifiable identification of the person as described in claim 1, wherein the physical feature captured by the optical physical recognition device is an iris scan.

7. A system for providing secure and verifiable identification of the person as described in claim 1, wherein the physical feature captured by the optical physical recognition device is a fingerprint.

8. A system for providing secure and verifiable identification of the person as described in claim 1, wherein the physical feature captured by the optical physical recognition device is a facial image of the person.

9. A system for providing secure and verifiable identification of the person as described in claim 1, wherein the system further comprises a visual display within the ambulance, wherein the visual display is configured to display the personal health related information received by the mobile computing device from the remote server.

10. A system for providing secure and verifiable identification of the person as described in claim 2, wherein the information about health insurance and advance directives associated with the person are configured to facilitate one or more treatments of the person by a healthcare professional.

\* \* \* \* \*